United States Patent [19]

Marvel et al.

[11] 3,935,167

[45] Jan. 27, 1976

[54] ACETYLENIC POLYMERS, TRIMERS THEREOF AND THE PRODUCTION THEREOF

[75] Inventors: Carl S. Marvel; Celeste Samyn, both of Tucson, Ariz.

[73] Assignee: University Patents, Inc., Stamford, Conn.

[22] Filed: June 6, 1974

[21] Appl. No.: 476,901

[52] U.S. Cl.................. 260/49; 260/63 R; 260/79; 260/79.3 R
[51] Int. Cl.². ........................................... C08G 75/00
[58] Field of Search.......... 260/79, 79.3 R, 49, 63 R

[56] References Cited
UNITED STATES PATENTS
3,532,677   10/1970   Baron ............................... 260/79.3
3,819,582   6/1974   Feasey ................................. 260/79

*Primary Examiner*—Melvyn I. Marquis
*Attorney, Agent, or Firm*—Mason, Kolehmainen, Rathburn & Wyss

[57] ABSTRACT

A polymer having one of the general formulae

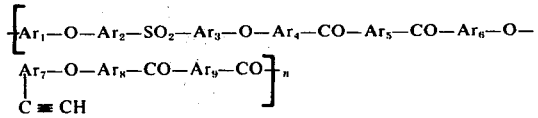

and

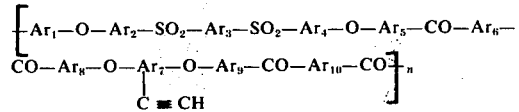

wherein $Ar_1$, $Ar_2$, $Ar_3$, $Ar_4$, $Ar_5$, $Ar_6$, $Ar_8$, $Ar_9$ and $Ar_{10}$ are the same or different bivalent aromatic hydrocarbon radicals containing six to ten carbon atoms, $Ar_7$ is a trivalent aromatic hydrocarbon radical containing 6 to 10 carbon atoms, and $n$ is 30 to 120.

8 Claims, 8 Drawing Figures

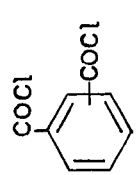
III
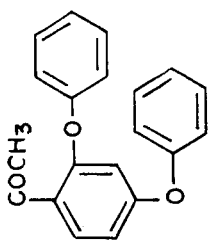
II
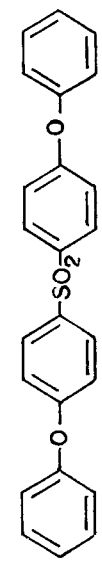
I
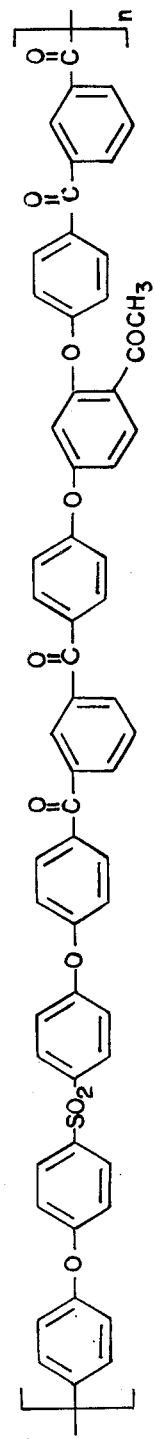
IV
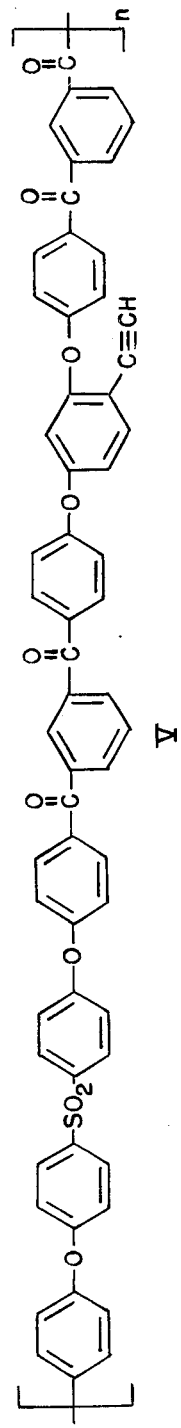
V

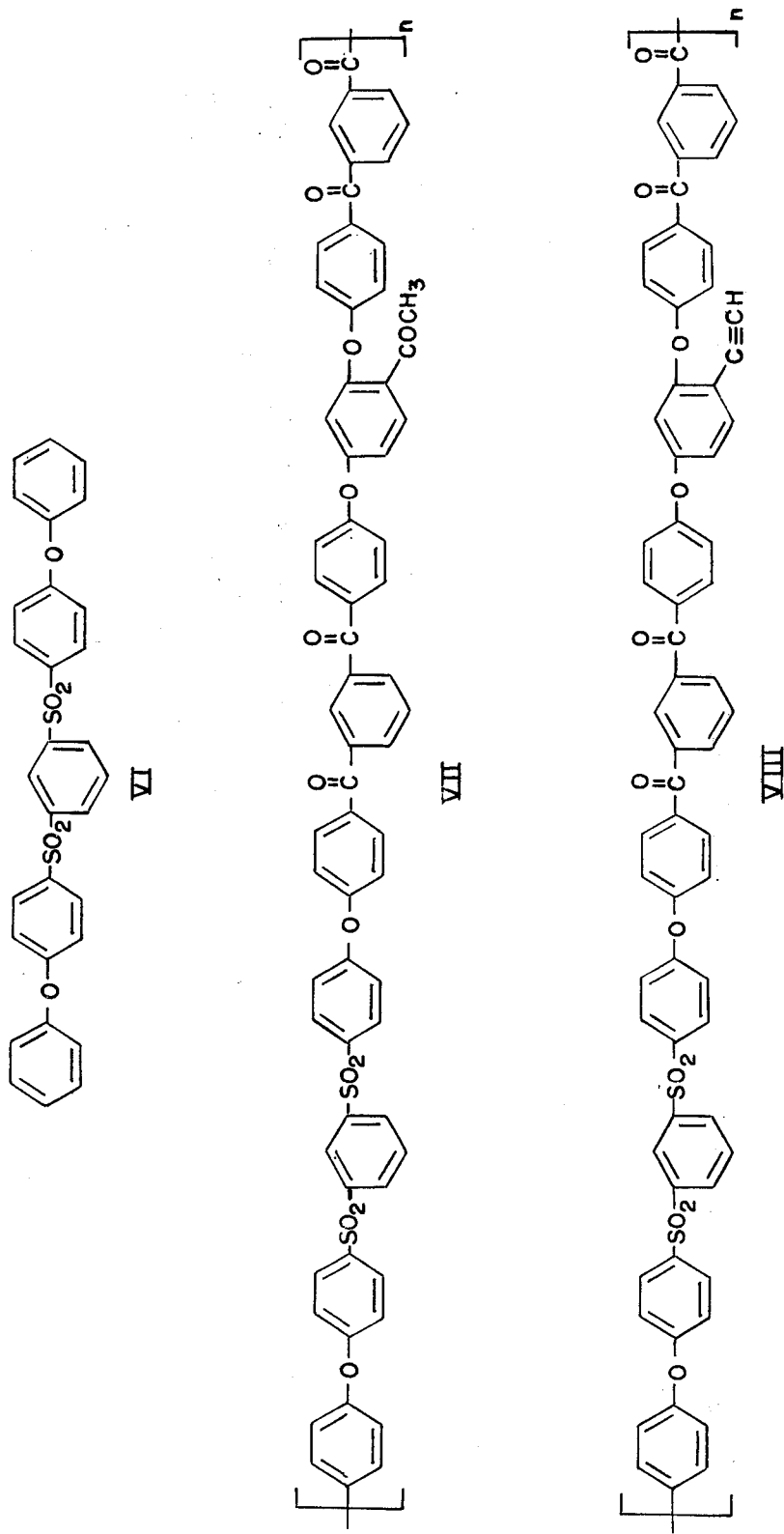

ACETYLENIC POLYMERS, TRIMERS THEREOF AND THE PRODUCTION THEREOF

This invention relates to organic polymers containing dangling acetylenic groups and to trimers of such acetylenic polymers. The invention also relates to methods of producing such polymers.

BACKGROUND OF THE INVENTION

Filled resins, e.g., glass fiber and fabric reinforced resins, are well known as suitable materials for forming structural units in the aircraft and other industries. A wide variety of resins have been proposed in the past for formulating such structures and as laminating resins for joining various materials. For example, polyester, epoxy and polycarbonate resins have been utilized as matrix resins for glass fiber-resin laminates. One of the difficulties experienced in the use of these resins, however, is that they are difficult to mold and mechanically work. Thus, it is often necessary to apply the resin in liquid form to the glass fibers on substrate to be laminated and then solidify the composite in order to obtain a suitable product. The resins previously used has to be melted or dissolved in a suitable solvent in order to achieve the desired liquid form. Many of these resins, however, decompose or suffer some deleterious chemical change when heated to temperatures sufficiently high to achieve melting. The result is a laminate or reinforced resin with reduced strength and physical properties.

Moreover, many of the previously used resins are insoluble in conventional volatile solvents. In addition, when forming laminates with solvent solutions of resins, it is necessary to employ special means for driving off and collecting those solvents which are capable of dissolving the resins but are relatively non-volatile.

In addition, the prior art matrix and laminating resins do not possess a sufficiently high degree of thermal stability which is requisite in many industrial applications.

It has been heretofore proposed to provide low melting laminating polymers. These polymers may be melted at low temperatures, contacted with the filler material or substrate to be laminated and cured or cross-linked to the resinous state. A serious disadvantage associated with these low-melting polymers, however, is that cross-linking involves a chemical reaction which liberates a volatile by-product such as carbon dioxide or water. The liberation of these reaction products operates to form voids in the resulting product. Obviously, the prior art low-melting laminating polymers may not be used in applications requiring close tolerance or uniform compositions throughout.

It is an object of the invention to provide low-melting polymers which may easily be admixed with fillers or contacted with substrates to be laminated and cross-linked to form a firmly bonded article having a uniform composition throughout.

It is a further object of the invention to provide novel reinforced and laminated resin compositions having high degrees of strength and thermal stability.

It is another object to provide low-melting polymers which may be crosslinked without the production of volatile materials.

A further object is to provide infusible crosslinked resins.

SUMMARY OF THE INVENTION

The above and other objects are achieved by providing low-melting polymers containing dangling acetylenic groups which are composed of 30 to 120 polymer units linked substantially linearly, said units being the reaction products of mixtures of diphenoxydiphenyl sulfone and diphenoxyacetophenone with an isophthaloyl or terephthaloyl halide, wherein the acetyl radical of the diphenoxy acetophenone moiety is thereafter converted to an ethynyl radical. The polymers so produced are relatively low-melting and are suitable for laminations. They are readily cured or cross-linked by heating at relatively low temperature to produce strong infusible resins. The cross-linking occurs by trimerization of the ethynyl radicals to produce stable benzenoid rings with polymeric side chains. The cross-linking takes place without the release of void-forming volatile materials.

When the acetylenic polymers of this invention are trimerized (cross-linked) while in contact with a filler or substrate to be laminated, the result is a product having a high degree of strength and thermal stability wherein the crosslinked polymer is firmly adhered to the filler or substrate.

GENERAL DESCRIPTION OF THE INVENTION

The linear polymers of this invention can be represented by one of the following general formulae:

$$\{Ar_1-O-Ar_2-SO_2-Ar_3-O-Ar_4-CO-Ar_5-CO-Ar_6-O-Ar_7-O-Ar_8-CO-Ar_9-CO\}_n$$
$$|$$
$$C \equiv CH$$

and

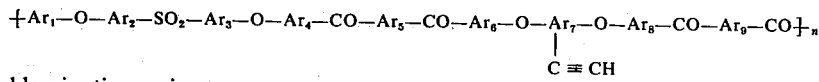

$$\{Ar_1-O-Ar_2-SO_2-Ar_3-SO_2-Ar_4-O-Ar_5-CO-Ar_6-CO-Ar_8-O-Ar_7-O-Ar_9-CO-Ar_{10}-CO\}_n$$
$$|$$
$$C \equiv CH$$

wherein $Ar_1$, $Ar_2$, $Ar_3$, $Ar_4$, $Ar_5$, $Ar_6$, $Ar_8$, $Ar_9$ and $Ar_{10}$ are the same or different bivalent aromatic hydrocarbon radicals containing 6 to 10 carbon atoms, $Ar_7$ is a trivalent aromatic hydrocarbon radical containing 6 to 10 carbon atoms, and $n$ is 30 to 120. $Ar_1$ through $Ar_6$ and $Ar_8$ through $Ar_{10}$ are ordinarily phenylene radicals, although they may also be tolylene, xylylene and naphthylene radicals. $Ar_7$ is usually a trivalent benzene radical but it can also be a trivalent radical derived from toluene, xylene or naphthalene.

The linear polymers described above can be trimerized to infusible, insoluble polymers. In the trimerization reaction, three ethynyl radicals are combined to form a benzenoid ring with three polymeric side chains.

In the foregoing general formulas, it should be understood that the sequence of the various aromatic radicals and oxy and sulfonyl linkages may vary from those illustrated. In other words, the sequence of the various moieties is random. The polymers are composed of various combinations of the bivalent radical from diphenoxydiphenyl sulfone (DPODPS) and the bivalent radical from diphenoxyacetophenone (DPOA) with amounts of the isophthaloyl and/or terephthaloyl radicals approximately equivalent to the total PDODPS and DPOA radicals. For example, the sequence could also be represented for a polymer produced from equivalent amounts of diphenoxydiphenyl sulfone (DPODPS) and diphenoxyacetophenone (DPOA) and two equivalents of isophthaloyl or terephthaloyl chloride as follows: $+$DPODPS—PHTH—DPODPS—PHTH—DPOAP—PHTH—DPOAP—PHTH$]_n$ where PHTH is a phthaloyl radical and n is 15 to 60.

BRIEF DESCRIPTION OF THE DRAWING

Reference is made to the attached drawings which illustrate by structural formula the starting materials and the polymers of this invention. In the drawings I represents diphenoxydiphenyl sulfone and II represents diphenoxyacetophenone. In forming the linear polymers, I and II are joined by Friedel-Crafts reaction with isophthaloyl or terephthaloyl chloride, represented by III. The result is a linear polymer represented by IV wherein $n$ can be an integer from 30 to 120. In this drawing the sequence of the radicals derived from I and II can be random, rather than regular as shown.

The acetyl radical in IV is then converted by an ethynyl radical as shown in V. This is preferably done by the Vilsmeyer reaction described below. The acetylenic polymer V can be trimerized by heating with a catalyst to produce a cross-linked polymer in which three radicals groups form a benzenoid ring, with polymer side chains extending therefrom.

In another embodiment of the invention, bis[phenoxybenzenesulfonyl]benzene, VI, is reacted with II and III to produce a polymer represented by VII. The acetyl radical of VII can be converted to an ethynyl radical as in VIII. Then VIII can be trimerized to a benzenoid ring with polymer side chains.

DETAILED DESCRIPTION OF THE INVENTION

In one preferred form, this invention comprises polymers with free (terminal) or dangling acetylenic (ethynyl) radicals, as well as the trimers thereof. These polymers preferably are produced from diphenoxydiphenyl sulfone (DPODPS) molecules and diphenoxyacetophenone (DPOA) molecules linked together in various combinations by isophthaloyl and/or terephthaloyl radicals in Friedel-Crafts polymerization with AlCl$_3$ catalyst. The mole ratio of DPODPS and DPOA molecules in the polymers can vary from 1:10 to 10:1. The amount of isophthaloyl and/or terephthaloyl radicals is preferably equivalent to the total moles of DPODPS and DPOA, and is in the range of 0.8 to 1.2 moles per total mole of DPODPS and DPOA. The acetyl radical of the acetophenone moiety is converted to an ethynyl radical by the Vilsmeyer reaction which comprises treating the acetyl-containing polymers with POCl$_3$ dissolved in dimethylformamide (DMF) which converts the acetyl radical to an alpha-chloro-beta-formyl-vinyl radical in 90% or higher yield. The latter is then treated with an alkaline reagent, such as NaOH in aqueous dioxane-dimethylformamide, lithium amide in DMF or KOH in DMF-ethanol, the latter reagent being preferred; by this treatment the alpha-chloro-beta-formylvinyl radical is converted in high yield (at least 90%) to an ethynyl radical. The polymer thus produced can be represented by structure V of the drawing.

In another preferred form, bis(phenoxybenzenesulfonyl)benzene (BPOBSB) replaces the DPODPS, the mole ratios being within the values given above. The acetylenic polymer so produced can be represented by structure IX of the drawing.

The polymers described above have average molecular weights from about 30,000 to 120,000 and can be represented by V and VIII, respectively, in the drawing, wherein n is a number between about 30 and 120. Such polymers are relatively low melting. At temperatures in the range of 180° to 225°C. they melt, flow easily and adhere to glass fibers. They are all soluble in DMF. They are thus useful as laminating resins. The acetylenic polymers represented by V and VIII all give excellent adhesion to glass fiber and produce homogeneous laminates with 33 wt % of polymer to glass fiber at one hour at 260°C. and 16,000 psi.

In a further preferred form of this invention, the polymers described above can be trimerized to form crosslinked polymers. The crosslinking can be catalyzed with 8–10% by weight of palladium chloride, palladium on charcoal, aluminum isopropoxide or nickelous cyanide at 230°C. for 24 hours and 285°C. for 24 hours. Crosslinking can also be induced by heat or can be done by cycloaddition a terephthalonitrile oxide or 9,10-dicyanoanthracene oxide in a suitable solvent such as sulfolane, followed by heating for 24 hours at 210°C, 24 hours at 250°C and 24 hours at 285°C. The crosslinked polymers are insoluble in solvents for the linear polymers.

Isothermal aging tests of the linear and crosslinked (cured) polymers were done in air. The weight losses are given in Table XIII. Most of the non-cured polymers show complete stability up to 300°C. Even at 350°C. the thermal stability of polymers A-III-2 (14 wt % acetylene component), A-IV-2 (11 wt % acetylene component) and A-V-2 (14 wt % acetylene component, 33% terephthaloyl chloride is very good. The lower the concentration of the acetylenic component the higher the thermal stability will be in the acetylene dangling polymers of structure V. The polymers of structure VIII (non-crosslinked) are less stable at 350°C. but at 300°C. most of them show complete thermal stability.

The polymers crosslinked with PdCl$_2$ are not oxidatively stable and give a serious loss of weight of 250°C. The acetylene polymers crosslinked by TPNO on the other hand are thermally stable at 250°C. and show fairly high thermal stability at 300°C. Above 350°C. they show great weight loss. Polymers cured by heating with aluminum isopropoxide are thermally and oxidatively stable to about 300°C.

EXAMPLE 1

Production of 2,4-Diphenoxyacetophenone 2,4-Diphenoxyacetophenone was prepared from 2,4-dichloroaniline by diazotation and Sandmeyer reaction with cuprous cyanide. On the reaction product was done a substitution of the chlorine with sodium phenolate and then a Grignard reaction with MeMgI which results in the formation of 2,4-diphenoxyacetophenone.

a. 2,4-Dichlorobenzonitrile 2,4-Dichloroaniline (42.5 g, 0.25 mole) was treated with 85 ml concentrated HCl and 85 ml H$_2$O. Under cooling 0°–5°C and stirring was added dropwise a solution of 24 g NaNO$_2$ in 50 ml H$_2$O. The diazonium chloride solution was then poured in small quantities to a solution of 40 g NaCN and 33 g CuCN in 200 ml $H_2O$ at 60°C. The temperature was kept between 60°–70°C while adding the diazonium salt solution. Then the 2,4-dichlorobenzonitrile was steam distilled. Recrystallization from MeOH; mp 59°C. Yield 22.5 g.

b. 2,4-Diphenoxybenzonitrile 2,4-Dichlorobenzonitrile (12.04 g, 0.07 mole) was treated with 17.8 g sodium phenolate (0.155 mole) in 100 ml DMSO at 100°–110°C during 48 hours under nitrogen and stirring. Then, the DMSO was evaporated and the residue was dissolved in ether. The ether solution was then washed with water. After evaporation of the ether, the product was recrystallized from MeOH. Yield 11.5 g; mp 85°–86°C.

c. 2,4-Diphenoxyacetophenone

To a Grignard solution of $CH_3MgI$ (0.14 mole) in 50 ml of anhydrous ether, was added a solution of 38.5 g, 2,4-diphenoxybenzonitrile in 350 ml dry benzene. After 48 hours reflux the complex was hydrolyzed. The ether-benzene solution was then washed out with water and dried over $Na_2SO_4$. After evaporation of the solvent, the product was distilled at 170°C under 0.025 mm pressure; yield 20 g.

EXAMPLE 2

Production of 4,4'-Diphenoxydiphenyl Sulfone

Bis-[4-chlorophenyl]sulfone (57.4 g), (0.2 mole) was reacted with 51 g sodium phenolate (0.44 mole) in 350 ml DMSO, under stirring and flushing with nitrogen for 48 hours at 110°C. The reaction mixture was then poured into 2 liters of water. The isolated product was then recrystallized from isopropanolchloroform. Yield 33 g, mp 141°–142°C.

EXAMPLE 3

Polymers from 4,4'-diphenoxydiphenyl sulfone and 2,4-diphenoxyacetophenone

Preparation of polymer A-I-2 (30 wt % acetylene component a. Preparation of acetyl polymer A-I-1

2,4-Diphenoxyacetophenone (0.8362 g, 2.75 mM), 4,4'-diphenoxydiphenyl sulfone (1.1055 g, 2.75 mM) and isophthaloyl chloride (1.1165 g, 5.5 mM) were dissolved in 40 ml dichloroethane. $AlCl_3$ (3.29 g) was added and the mixture stirred under nitrogen atmosphere at room temperature during 24 hours. The precipitate was then filtered off, washed several times with methanol in a blender and dried. Yield 2.42 g, mp 205°–225°C, inherent viscosity 0.234 at 30°C in DMF. This polymer has general structure IV.

b. Preparation of beta-chloroaldehyde A-I-C

A solution of 2.168 g acetyl polymer A-I-1 in 110 ml DMF (dry) was added to a freshly prepared solution of Vilsmeyer reagent. The Vilsmeyer reagent was made by adding $POCl_3$ to cold DMF and this solution was stirred for a further two hour under cooling. For 1 mM of acetyl component there is used three ml Vilsmeyer reagent (1 ml $POCl_3$ in 2 ml DMF).

c. Preparation of polymer A-I-2

To a solution of 0.252 g KOH in 10 ml ethanol and 20 ml of DMF at 80°C was added a solution of the previous beta-chloroaldehyde (1.876 g in 90 ml DMF). After complete addition the reaction mixture was stirred for a complete reaction time of 75 minutes at 80°C. The polymer was then precipitated in distilled water which contained some acetic acid. Yield 1.66 g mp 195°–210°C, inherent viscosity 0.168 at 30°C in DMF. The polymer has general structure V.

EXAMPLE 4

Preparation of polymer A-II-2 (19 wt % acetylene component)

a. Preparation of polymer A-II-1

2,4-Diphenoxyacetophenone (0.3954 g, 1.3 mM), 4,4'-diphenoxydiphenyl sulfone (1.0452 g, 2.6 mM) and isophthaloyl chloride (0.7917 g, 3.9 mM) were dissolved in 30 ml dichloroethane. $AlCl_3$ (2.26 g) was added and the mixture stirred under nitrogen atmosphere at room temperature during 24 hours. The precipitate was then filtered off and washed several times with MeOH in a blender and dried. Yield 1.82 g, mp 195°–215°C, inherent viscosity 0.179 in DMF at 30°C. The polymer has general structure IV.

b. Preparation of beta-chloroaldehyde A-II-C

A solution of 1.534 g acetyl polymer A-II-1 in 75 ml DMF was added to three ml Vilsmeyer reagent (1 ml $POCl_3$ in 2 ml DMF). The reaction was then continued and worked up as for polymer A-I-C, mp 185°–200°C. Yield 1.400 g.

c. Preparation of polymer A-II-2

To a solution of 70 mg KOH in 5 ml ethanol and 10 ml of DMF at 80°C was added a solution of the previous beta-chloroaldehyde (0.769 g in 40 ml DMF). The reaction was continued and worked up as for polymer A-I-2. Yield 0.67 g, mp 185°–200°C, inherent viscosity 0.161 at 30°C in DMF. The polymer has general structure V.

EXAMPLE 5

Preparation of polymer A-III-2 (14 wt % acetylene component)

a. Preparation of polymer A-III-1

2,4-diphenoxyacetophenone (0.4729 g, 1.55 mM), 4,4'-diphenoxydiphenyl sulfone (1.8693, 4.65 mM) and isophthaloyl chloride (1.2586 g, 6.2 mM) were dissolved in 50 ml dichloroethane. $AlCl_3$ (3.60 g) was added and the reaction worked up as for polymer A-I-1. Yield 2.70 g, mp 200°–220°C, inherent viscosity 0.244 at 30°C in DMF. The polymer has general structure IV.

b. Preparation of beta-chloroaldehyde A-III-C

A solution of polymer A-III-1 (2.400 g in 120 ml DMF) was added to a freshly prepared solution of Vilsmeyer reagent and worked up as for polymer A-I-C. Yield 2.250 g, mp 175°–195°C.

c. Preparation of polymer A-III-2

To a solution of 0.150 g KOH in 10 ml ethanol and 20 ml DMF at 80°C is added a solution of the previous beta-chloroaldehyde (2.212 g in 120 ml DMF). The reaction was then worked up as for polymer A-I-2. Yield 1.956 g, mp 180°–195°C, inherent viscosity 0.168. The polymer has general structure V.

EXAMPLE 6

Preparation of polymer A-IV-2 (11 wt % acetylene component)

a. Preparation of polymer A-IV-1

2,4-Diphenoxyacetophenone (0.2633 g, 0.866 mM), 4,4'-diphenoxydiphenyl sulfone (1.3925 g, 3.46 mM) and isophthaloyl chloride (0.8789 g, 4.33 mM) were dissolved in 35 ml dichloroethane. $AlCl_3$ (2.54 g) was added and the reaction worked up as for polymer A-I-1. Yield 2 g, mp 200°–220°C, inherent viscosity 0.264 at 30°C in DMF.

b. Preparation of beta-chloroaldehyde A-IV-C

A solution of 1.800 g polymer A-IV-1 in 90 ml DMF was added to the freshly prepared Vilsmeyer reagent and worked up as for polymer A-I-C. Yield 1.700 g, mp 175°–190°C.

c. Preparation of polymer A-IV-2

To a solution of 0.090 g KOH in 5 ml ethanol and 10 ml DMF at 80°C was added to a solution of the previous beta-chloroaldehyde (1.664 g in 80 ml DMF). The reaction was then worked up as for polymer A-I-2. Yield 1.449 g, mp 185°–200°C, inherent viscosity 0.176 at 30°C in DMF. The polymer has general structure V.

EXAMPLE 7

Preparation of polymer A-V-2 (14 wt % acetylene component)

a. Preparation of polymer A-V-1

2,4-Diphenoxyacetophenone (0.3926 g, 1.291 mM), 4,4'-diphenoxydiphenyl sulfone (1.5569 g, 3.813 mM), isophthaloyl chloride (0.6906 g, 2.402 mM) and terephthaloyl chloride (0.3453 g, 1.701 mM) were dissolved in 80 ml dichloroethane. $AlCl_3$ (3.04 g) was added and worked up as for polymer A-I-1. Yield 2.228 g, mp 195°–215°C, inherent viscosity 0.216 at 30°C in DMF.

b. Preparation of beta-chloroaldehyde A-V-C

A solution of polymer A-V-1 (2.020 g in 100 ml DMF was added to the freshly prepared Vilsmeyer reagent and worked up as for polymer A-I-C. Yield 1.86 g, mp 185°–205°C.

c. Preparation of polymer A-V-2

To a solution of 0.118 g KOH in 5 ml ethanol and 10 ml DMF at 80°C was added a solution of the previous beta-chloroaldehyde (1.740 g in 85 ml DMF). The reaction was then worked up as for polymer A-I-2. Yield 1.418 g, mp 185°–205°C, inherent viscosity 0.183 at 30°C in DMF. The polymer is type V.

EXAMPLE 8

1,3-Bis-[p-phenoxybenzenesulfonyl]benzene 1,3-m-Benzenedisulfonyl chloride (65 g) was dissolved in 750 ml of dry diphenyl ether. A portion of 2.5 g sublimed $FeCl_3$ was added, and the mixture was stirred under nitrogen at 140°C for 15 hours. The mixture was washed with water and then dried over $Na_2SO_4$. The excess of diphenyl ether was distilled off under vacuum and the residue was distilled via a short path (bp 400°–420°C/0.06 mm). The glassy solid was dissolved in 100 ml of $CHCl_3$ and precipitated as a white powder in 1 liter of diethyl ether; mp 142°–143°C.

EXAMPLE 9

Preparation of polymer B-I-2 (26 wt % acetylene component)

a. Preparation of polymer B-I-1

2,4-Diphenoxyacetophenone (0.900 g, 2.96 mM), 1,3-bis-[p-phenoxybenzenesulfonyl]benzene (1.640 g, 2.96 mM) and isophthaloyl chloride (1.201 g, 5.92 mM) were dissolved in 50 ml dichloroethane. $AlCl_3$ (3.99 g) was added and the mixture stirred under nitrogen atmosphere at room temperature during 24 hours. The precipitate was then filtered off, washed several times with methanol in a blender and dried. Yield 3.025 g, mp 190°–210°C, inherent viscosity 0.165 at 30°C in DMF. The polymer has general structure VII.

b. Preparation of beta-chloroaldehyde B-I-C

A solution of polymer B-I-1 (1.815 g in 90 ml DMF) was added to a freshly prepared solution of Vilsmeyer reagent and worked up as for polymer A-I-C. Yield 1.710 g, mp 180°–195°C.

c. Preparation of polymer B-I-2

To a solution of 0.210 g KOH in 10 ml ethanol and 20 ml DMF at 80°C was added a solution of the previous beta-chloroaldehyde (1.612 g in 75 ml DMF). The reaction was then worked up as for polymer A-I-2. Yield 1.33 g, mp 185°–205°C, inherent viscosity 0.132 at 30°C in DMF. The polymer has general structure VIII.

EXAMPLE 10

Preparation of polymer B-II-2 (16 wt % acetylene component)

a. Preparation of polymer B-II-1

2,4-Diphenoxyacetophenone (0.3945 g, 1.29 mM), 1,3-bis-[p-phenoxybenzenesulfonyl]benzene (1.398 g, 2.58 mM) and isophthaloyl chloride (0.7856 g, 3.87 mM) were dissolved in 35 ml dichloroethane. $AlCl_3$ (2.58 g) was added and the reaction worked up as for polymer B-I-1. Yield 1.94 g, mp 195°–215°C, inherent viscosity 0.14 at 30°C in DMF. The polymer has general structure VII.

b. Preparation of beta-chloroaldehyde B-II-C

A solution of polymer B-II-1 (1.600 g in 70 ml DMF) was added to a freshly prepared solution of Vilsmeyer reagent and worked up as for polymer A-I-C. Yield 1.470 g, mp 170°–190°C.

c. Preparation of polymer B-II-2

To a solution of 0.091 g KOH in 5 ml ethanol and 10 ml DMF at 80°C was added a solution of the previous beta-chloroaldehyde (1.184 g in 60 ml DMF). The reaction was worked up as for polymer A-I-2. Yield 1.058 g, mp 175°–190°C, inherent viscosity 0.124 at 30°C in DMF. The polymer has general structure VIII.

EXAMPLE 11

Preparation of polymer B-III-2 (11 wt % acetylene component)

a. Preparation of polymer B-III-1

2,4-Diphenoxyacetophenone (0.4363 g, 1.4 mM), 1,3-bis[p-phenoxybenzenesulfonyl]benzene (2.2764 g, 4.2 mM) and isophthaloyl chloride (1.1368 g, 5.6 mM) were dissolved in 80 ml dichloroethane. $AlCl_3$ (3.72 g) was added and the reaction worked up as for polymer B-I-1. Yield 3,235 g, mp 210°–225°C, inherent viscosity 0.182 at 30°C in DMF.

b. Preparation of beta-chloroaldehyde B-III-C

A solution of polymer B-III-1 (2.800 g in 130 ml DMF) was added to a freshly prepared solution of Vilsmeyer reagent and worked up as for polymer A-I-C. Yield 2.65 g, mp 185°–205°C.

c. Preparation of polymer B-III-2

To a solution of 0.145 g KOH in 10 ml ethanol and 20 ml DMF at 80°C was added a solution of the previous beta-chloroaldehyde (2.519 g in 120 ml DMF). The reaction was worked up as for polymer A-I-2. Yield 2.09 g, mp 195°–210°C, inherent viscosity 0.143 at 30°C in DMF. The polymer is type VIII.

EXAMPLE 12

Preparation of polymer B-IV-2 (9 wt % acetylene component)

a. Preparation of polymer B-IV-1

2,4-Diphenoxyacetophenone (0.2895 g, 0.95 mM), 1,3-bis-[p-phenoxybenzenesulfonyl]benzene (2.0596 g, 3.8 mM) and isophthaloyl chloride (0.9642 g, 4.75 mM) were dissolved in 40 ml dichloroethane. $AlCl_3$ (3.15 g) was added and the reaction worked up as for polymer B-I-1. Yield 2.80 g, mp 210°–225°C, inherent viscosity 0.171 at 30°C in DMF.

b. Preparation of beta-chloroaldehyde B-IV-C

A solution of polymer B-IV-1 (2.600 g in 130 ml DMF) was added to a freshly prepared solution of Vilsmeyer reagent and worked up as for polymer A-I-C. Yield 2.42 g, mp 195°–210°C.

c. Preparation of polymer B-IV-2

To a solution of 0.105 g KOH in 5 ml ethanol and 10 ml DMF at 80°C was added a solution of the previous beta-chloroaldehyde (2.247 g in 120 ml DMF). The reaction was worked up as for polymer A-I-2. Yield 1.82 g, mp 195°–210°C, inherent viscosity 0.15 at 30°C in DMF. The polymer is type VIII.

EXAMPLE 13

Preparation of polymer B-V-2 (26 wt % acetylene component)

a. Preparation of polymer B-V-1

2,4-Diphenoxyacetophenone (0.6768 g, 2.22 mM), 1,3-bis-[p-phenoxybenzenesulfonyl]benzene (1.203 g, 2.22 mM), isophthaloyl chloride (0.6008 g, 2.96 mM), and terephthaloyl chloride (0.3004 g, 1.48 mM) were dissolved in 40 ml dichloroethane. $AlCl_3$ (2.95 g) was added and the reaction worked up as for polymer B-I-1. Yield 2.157 g, mp 190-210°C, inherent viscosity 0.165 at 30°C in DMF.

b. Preparation of beta-chloroaldehyde B-V-C

A solution of polymer B-V-1 (1.835 g in 75 ml DMF) was added to a freshly prepared solution of Vilsmeyer reagent and worked up as for polymer A-I-C. Yield 1.650 g, mp 175°–195°C.

c. Preparation of polymer B-V-2

To a solution of 0.057 g KOH in 5 ml ethanol and 5 ml DMF at 80°C was added a solution of the previous beta-chloroaldehyde (0.780 g in 40 ml DMF). The reaction was worked up as for polymer A-I-2. Yield 0.703 g, mp 180°–195°C, inherent viscosity 0.143 at 30°C in DMF. The polymer is type VIII.

EXAMPLE 14

Preparation of polymer B-VI-2 (11 wt % acetylene component)

a. Preparation of polymer B-VI-1

2,4-Diphenoxyacetophenone (0.3421 g, 1.125 mM), 1,3-bis-[p-phenoxybenzenesulfonyl]benzene (1.829 g, 3.375 mM), isophthaloyl chloride (0.609 g, 3 mM) and terephthaloyl chloride (0.3045 g, 1.5 mM) were dissolved in 40 ml dichloroethane. $AlCl_3$ (2.99 g) was added and the reaction worked up as for polymer B-I-1. Yield 2.184 g, mp 200°–220°C, inherent viscosity 0.176 at 30°C in DMF.

b. Preparation of beta-chloroaldehyde B-VI-C

A solution of polymer B-VI-1 (2 g in 100 ml DMF) was added to a freshly prepared solution of Vilsmeyer reagent and worked up as for polymer A-I-C. Yield 1.9 g, mp 185°–200°C.

c. Preparation of polymer B-VI-2

To a solution of 0.098 g KOH in 5 ml ethanol and 10 ml DMF at 80°C was added a solution of the previous beta-chloroaldehyde (1.758 g in 80 ml DMF). The reaction was worked up as for polymer A-I-2. Yield 1.6 g, mp 185°–205°C, inherent viscosity 0.146 at 30°C in DMF. The polymer is type VIII.

EXAMPLE 15

Preparation of polymer A-VI-2 (6 wt % acetylene component)

a. Preparation of polymer A-VI-1

2,4-Diphenoxyacetophenone (0.2603 g, 0.856 mM), 4,4'-diphenoxydiphenyl sulfone (2.7535 g, 6.85 mM) and isophthaloyl chloride (1.5643 g, 7.706 mM) were dissolved in 60 ml dichloroethane. $AlCl_3$ (4.80 g) was added and the mixture stirred under nitrogen atmosphere at room temperature during 24 hours. The precipitate was then filtered off and washed several times with MeOH in a blender and dried. Yield 3.86 g, mp 225°–245°C, inherent viscosity 0.728 in $H_2SO_4$ at 30°C. The polymer has general structure IV.

b. Preparation of beta-chloroaldehyde A-VI-C

A solution of 3.225 g acetyl polymer A-VI-1 in 160 ml DMF was added to a freshly prepared solution of Vilsmeyer reagent and worked up as for polymer A-I-C. Yield 3.160 g, mp 210°–230°C.

c. Preparation of polymer A-VI-2

To a solution of 0.085 g KOH in 5 ml ethanol and 20 ml DMF at 80°C is added a solution of the previous beta-chloroaldehyde (2.857 g in 140 ml DMF). The reaction was then worked up as for polymer A-I-2. Yield 2.48 g, mp 205°–225°C, inherent viscosity 0.285 in DMF at 30°C and 0.429 in HMPA at 30°C.

EXAMPLE 16 a. Curing of polymer A-I-2 with terephthalonitrile oxide (TNPO)

Acetylenic polymer A-I-2 (0.650 g) was dissolved in 25 ml sulfolane (dry) by heating at 60°–70°C. Then 0.160 g TPNO was added and the reaction mixture stirred for one hour at room temperature. Another 0.160 g TPNO was then added and stirring was continued for a further 2 hours at 60°C. The reaction was then poured into methanol and the precipitate was filtered off and washed out with MeOH, then dried. The dry product (0.830 g) was then cured in an aluminum foil under nitrogen, 24 hours at 210°C and 48 hours at 285°C. The residue was then taken up in DMF and stirred overnight. After filtration and drying the same weight of product was recovered so that the cured product was 100% insoluble in DMF.

b. Curing of polymer A-I-2 with 8 wt % $PdCl_2$

A well ground mixture of 0.842 g polymer A-I-2 and 8 wt % $PdCl_2$ was heated 24 hours at 210°C and 48 hours at 285°C, in an aluminum foil under nitrogen. The black-brown residue was then treated with diluted HCl for 24 hours. After filtration and washing out with water it was dried. Then, it was taken up in DMF and stirred overnight; 4.1% was soluble and 95.9% insoluble.

c. Curing of polymer A-III-2 with TPNO

Acetylenic polymer A-III-2 (0.600 g) was dissolved in 25 ml sulfolane (dry) by heating at 60°–70°C. Then 30 mg TPNO was added and the reaction mixture stirred for one hour at room temperature. Another 30 mg TPNO was then added and stirring was continued for a further hour at 50°C. The reaction was then conducted as for curing polymer A-I-2. The isolated product (0.535 g) was then heated under nitrogen, 24 hours at 210°C, 24 hours at 250°C and 24 hours at 285°C. The residue was then treated with DMF overnight, filtered and dried. There remained an 88.9% yield of a polymer which was insoluble in DMF.

d. Curing of polymer B-I-2 with 8 wt % $PdCl_2$

A well ground mixture of polymer B-I-2 (0.6935 g) and 8 wt % $PdCl_2$ was heated 24 hours at 210°C and 48 hours at 285°C, in an aluminum foil under nitrogen. The residue was then treated with diluted HCl for 24 hours, it was then filtered, washed out and dried. 98.2% was insoluble in DMF.

e. Curing of polymer B-III-2 with 8 wt % $PdCl_2$

A well ground mixture of polymer B-III-2 (0.6711 g) and 8 wt % $PdCl_2$ was heated and treated in the same circumstances as previous sample. There was 90.5% insoluble material left after stirring up the residue overnight with DMF.

f. Curing of polymer B-IV-2 with TPNO

Acetylenic polymer B-IV-2 (0.776 g) was dissolved in 25 ml sulfolane (dry) by heating at 60°–70°C. Then 0.180 g TPNO was added and the reaction mixture stirred for one hour at room temperature. Another 0.180 g TPNO was then added and the reaction continued and worked up as for polymer A-I-2. After treating the residue with DMF there remained 97.3% insoluble material.

g. Curing of polymer A-VI-2 with 9 wt % $Al(OC_3H_7)_3$

A well ground mixture of polymer A-VI-2 (0.218 g) and 9 wt % Al isopropoxide was heated 24 hours at 230°C and 24 hours at 285°C, in an aluminum foil under nitrogen. The residue was then treated with diluted HCl overnight, it was then filtered, washed out and dried. 72% was insoluble in DMF.

h. Curing of polymer A-II-2 with 9 wt % $Al(OC_3H_7)_3$

A well ground mixture of polymer A-II-2 (0.304 g) and 9 wt % Al isopropoxide was heated and worked up as in previous procedure. 89% insoluble in DMF.

i. Curing of polymer A-VI-2 with 10 wt % Pd/C

A well ground mixture of polymer A-VI-2 (0.285 g) and 10 wt % Pd/C was heated and worked up as in previous procedure. 79% insoluble in DMF.

j. Curing of polymer B-VI-2 with ATNO

Acetylenic polymer B-VI-2 (0.486 g) was dissolved in 25 ml sulfolane by heating. Then 14 mg ATNO (anthracene-9,10-dinitrileoxide) was added and the reaction mixture stirred for 2 hours at 70°C. The reaction was then worked up as for curing polymer A-I-2 with TPNO. The isolated product was then heated under nitrogen, 24 hours at 210°C, 24 hours at 250°C and 24 hours at 285°C. The residue was then treated with DMF overnight, filtered and dried. There remained 89% insoluble in DMF.

EXAMPLE 17

Isothermal Aging Experiments a. An isothermal aging experiment of CS-I-A-CT, obtained by curing polymer A-I-2 (30 wt % acetylenic component) with TPNO gave the following results for loss of weight: 7 days at 300°C, 6% loss and no loss of weight at 250°C.

b. An isothermal aging experiment of CS-3-A-CT, obtained by polymer A-III-2 (14 wt % acetylenic component) with terephthalonitrile-N,N′-oxide under nitrogen, gave the following results of loss of weight:

3 days at 275°C, 3% loss; 7 days at 275°C, 3.7% loss;
5 days at 300°C, 6.5% loss; 7 days at 300°C, 8.8% loss.

c. Polymer A-IV-2 was cured by heating under nitrogen 48 hours at 320°C. This polymer has 11 wt % acetylenic component and the cured polymer was 100% insoluble in DMF.

d. An isothermal aging experiment of the polymer obtained by trimerizing B-VI-2 (11 wt % acetylenic component) with anthracene-9,10-bis-nitrile oxide under nitrogen, gave the following results for loss of weight:

3 days at 275°C, 4.7% loss; 7 days at 275°C, 5.7% loss;
5 days at 300°C, 9.9% loss; 7 days at 300°C, 11.2% loss.

e. An isothermal aging experiment CS-6-AA obtained by curing polymer A-VI-2 (6 wt % acetylenic component) with aluminum isopropoxide, gave the following results for loss of weight: 7 days at 250°C, 2.1% loss; 4 days at 275°C, 3.4% loss.

f. An isothermal aging experiment CS-2-AA obtained by curing polymer A-II-2 (19 wt % acetylenic component) with aluminum isopropoxide, gave the following results for loss of weight: 7 days at 250°C, 0.2% loss; 4 days at 275°C, 2.5% loss.

The inherent viscosities in $H_2SO_4$ for the acetyl polymers and in HMPA for the acetylene polymers were as follows:

Acetyl polymers: inherent viscosity in $H_2SO_4$ at 30°C

| | | | |
|---|---|---|---|
| A-I-1 | 0.391 | B-I-1 | 0.251 |
| A-II-1 | 0.358 | B-II-1 | 0.229 |
| A-III-1 | 0.434 | B-III-1 | 0.331 |
| A-IV-1 | 0.479 | B-IV-1 | 0.304 |
| | | B-V-1 | 0.225 |
| | | B-VI-1 | 0.280 |

Acetylene polymers: inherent viscosity in HMPA at 30°C

| | | | |
|---|---|---|---|
| A-I-2 | 0.22 | B-I-2 | 0.18 |
| A-II-2 | 0.206 | B-II-2 | 0.181 |
| A-III-2 | 0.219 | B-III-2 | 0.185 |
| A-IV-2 | 0.23 | B-IV-2 | 0.222 |
| A-V-2 | 0.216 | B-V-2 | 0.183 |
| A-VI-2 | 0.429 | B-VI-2 | 0.201 |

TABLE VIII

POLYMERS FROM 2,4-DIPHENOXYACETOPHENONE AND 4,4′-DIPHENOXYDIPHENYL SULFONE

| Polymer | IPC[a] | TPC[b] | DPA[c] | DPDPS[d] | Inherent viscosity[e] | mp°C |
|---|---|---|---|---|---|---|
| A-I-1 | 5.5 | — | 2.75 | 2.75 | 0.234 | 205–225 |
| A-II-1 | 3.43 | — | 1.44 | 2.88 | 0.179 | 195–215 |
| A-III-1 | 6.20 | — | 1.55 | 4.65 | 0.244 | 200–220 |
| A-IV-1 | 4.33 | — | 0.866 | 3.46 | 0.264 | 200–220 |
| A-V-1 | 3.40 | 1.70 | 1.29 | 3.81 | 0.216 | 195–215 |

[a]Millimoles of isophthaloyl chloride
[b]Millimoles of terephthaloyl chloride
[c]Millimoles of 2,4-diphenoxyacetophenone
[d]Millimoles of 4,4′-diphenoxydiphenyl sulfone
[e]In DMF (0.5 g/100 ml) at 30°C

TABLE IX

POLYMERS FROM 2,4-DIPHENOXYACETOPHENONE AND
1,3-bis-[p-PHENOXYBENZENESULFONYL]BENZENE

| Polymer | IPC[a] | TPC[b] | DPA[c] | BPBSB[d] | Inherent viscosity[e] | mp°C |
|---|---|---|---|---|---|---|
| B-I-1 | 4.22 | — | 2.11 | 2.11 | 0.165 | 190–210 |
| B-II-1 | 3.87 | — | 1.29 | 2.58 | 0.14 | 195–215 |
| B-III-1 | 5.60 | — | 1.40 | 4.20 | 0.182 | 210–225 |
| B-IV-1 | 4.75 | — | 0.95 | 3.80 | 0.171 | 210–225 |
| B-V-1 | 2.96 | 1.48 | 2.22 | 2.22 | 0.165 | 190–210 |
| B-VI-1 | 3.0 | 1.50 | 1.12 | 3.37 | 0.176 | 200–220 |

[a]Millimoles of isophthaloyl chloride
[b]Millimoles of terephthaloyl chloride
[c]Millimoles of 2,4-diphenoxyacetophenone
[d]Millimoles of 1,3-bis-[p-phenoxybenzenesulfonyl]benzene
[e]In DMF (0.5 g/100 ml) at 30°C

TABLE X

ACETYLENE POLYMERS FROM DIPHENOXYPHENYL SULFONE

| Polymer | Inherent viscosity[a] | mp°C |
|---|---|---|
| A-I-2 | 0.168 | 195–210 |
| A-II-2 | 0.161 | 180–195 |
| A-III-2 | 0.168 | 180–195 |
| A-IV-2 | 0.176 | 185–200 |
| A-V-2 | 0.183 | 185–205 |

[a]In DMF (0.5 g/100 ml) at 30°C

TABLE XI

ACETYLENE POLYMERS FROM BIS[PHENOXYBENZENESULFONYL]BENZENE

| Polymer | Inherent viscosity[a] | mp°C |
|---|---|---|
| B-I-2 | 0.132 | 185–205 |
| B-II-2 | 0.124 | 175–190 |
| B-III-2 | 0.143 | 195–210 |
| B-IV-2 | 0.150 | 195–210 |
| B-V-2 | 0.143 | 180–195 |
| B-VI-2 | 0.146 | 185–205 |

[a]In DMF (0.5 g/100 ml) at 30°C

TABLE XII

CROSSLINKING EXPERIMENTS

| Polymer | Cross-linked Polymer | Catalyst | % Cross-linked Polymer (insoluble product) |
|---|---|---|---|
| A-I-2 | CS-1-A-CP | PdCl$_2$ | 95.9 |
| A-I-2 | CS-1-A-CT | TPNO | 100 |
| A-III-2 | CS-3-A-CT | TPNO | 88.9 |
| B-I-2 | CS-1-B-CP | PdCl$_2$ | 98.2 |
| B-III-2 | CS-3-B-CP | PdCl$_2$ | 90.5 |
| B-IV-2 | CS-4-B-CT | TPNO | 97.3 |

TABLE XIII

ISOTHERMAL AGING OF NON-CURED AND CURED ACETYLENE POLYMERS

| Polymer | 7 days at 250°C | 7 days at 300°C | 4 days at 350°C |
|---|---|---|---|
| A-I-2 | no | 2 | 42.7 |
| A-II-2 | no | no | 10.3 |
| A-III-2 | no | 0.7 | 4.9 |
| A-IV-2 | no | no | 2.1 |
| A-V-2 | no | no | 5.8 |
| B-I-2 | no | no | 23.3 |
| B-II-2 | no | 5.2 | 46.4 |
| B-III-2 | no | no | 8.1 |
| B-IV-2 | no | no | 10.4 |
| B-V-2 | no | 2.7 | 19.4 |
| B-VI-2 | no | no | 11.6 |
| CS-1-A-CP | 16.4 | 38.8 | 85 |
| CS-1-A-CT | no | 7.2 | 64 |
| CS-1-B-CP | 11.7 | 40 | 83 |
| CS-3-B-CP | 24.6 | — | 88 |
| CS-4-B-CT | no | 6 | 58 |

Percent loss of weight

In this specification, the following abbreviations are used:

DMAc = dimethylacetamide
DMF = dimethylformamide
DMSO — dimethyl sulfoxide
g = gram(s)
HMPA = hexamethylphosphoric triamide
hr = hour(s)
IPC = isophthaloyl chloride
Me = methyl
MeOH = methanol
ml = milliliter(s)
mm = millimeter(s) (of mercury)
mM = millimole(s)
mp = melting point
TGA = thermogravimetric analysis
TPC = terephthaloyl chloride
TPNO = teraphthalonitrile oxide
Vilsmeyer reagent = 1 ml of POCl$_3$ in 2 ml of DMF

We claim:

1. A polymer having one of the general formulae

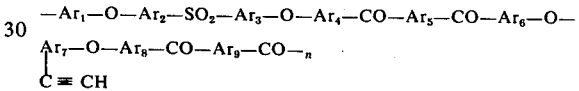

and

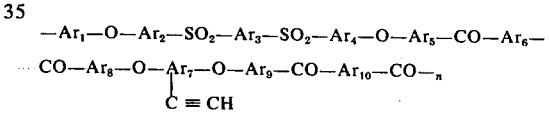

wherein Ar$_1$, Ar$_2$, Ar$_3$, Ar$_4$, Ar$_5$, Ar$_6$, Ar$_8$, Ar$_9$ and Ar$_{10}$ are the same or different bivalent aromatic hydrocarbon radicals containing 6 to 10 carbon atoms, Ar$_7$ is a trivalent aromatic hydrocarbon radical containing 6 to 10 carbon atoms, and $n$ is 30 to 120.

2. A polymer of claim 1 wherein Ar$_1$, Ar$_2$, Ar$_3$, Ar$_4$, Ar$_5$, Ar$_6$, Ar$_7$, Ar$_8$, Ar$_9$ and Ar$_{10}$ each contain 6 carbon atoms.

3. A polymer produced by Friedel-Crafts polymerization of diphenoxyacetophenone and diphenoxydiphenyl sulfone with an acid chloride selected from the group consisting of isophthaloyl chloride and terephthaloyl chloride.

4. A polymer as defined by claim 3 wherein the acetyl radical of the diphenoxyacetophenone moiety is converted to an ethynyl radical.

5. A polymer produced by Friedel-Crafts polymerization of diphenoxyacetophenone and bis(phenoxybenzenesulfonyl)benzene with an acid chloride selected from the group consisting of isophthaloyl chloride and terephthaloyl chloride.

6. A polymer as defined by claim 5 wherein the acetyl radical of the diphenoxyacetophenone moiety is converted to an ethynyl radical.

7. A crosslinked polymer formed by the trimerization of an ethynyl radical of a polymer as defined by claim 1.

8. A crosslinked polymer formed by the trimerization of an ethynyl radical of a polymer as defined by claim 2.

* * * * *

PO-1050
(5/69)

UNITED STATES PATENT OFFICE
CERTIFICATE OF CORRECTION

Patent No. 3,935,167                    Dated January 27, 1976

Inventor(s) Carl S. Marvel, Celeste Samyn

It is certified that error appears in the above-identified patent and that said Letters Patent are hereby corrected as shown below:

Column 14, after line 25, in claim 1, the formulae should read as follows:

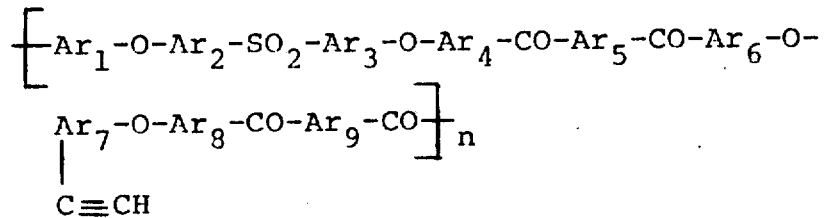

and

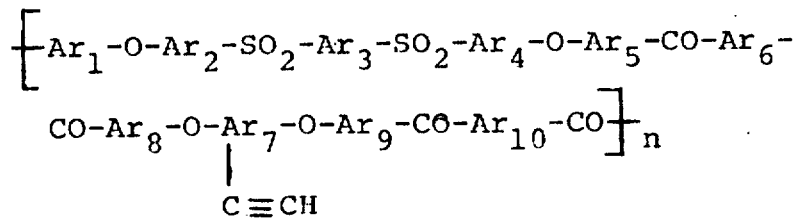

Signed and Sealed this twenty-fifth Day of May 1976

[SEAL]

Attest:

RUTH C. MASON
Attesting Officer

C. MARSHALL DANN
Commissioner of Patents and Trademarks